United States Patent
Hicks et al.

(10) Patent No.: US 8,658,094 B2
(45) Date of Patent: *Feb. 25, 2014

(54) HIGH TEMPERATURE AND PRESSURE OXIDATION-REDUCTION POTENTIAL MEASURING AND MONITORING DEVICE FOR HOT WATER SYSTEMS

(75) Inventors: Peter D. Hicks, Aurora, IL (US); M. Alexandra Knoth, Aurora, IL (US)

(73) Assignee: Nalco Company, Naperville, IL (US)

(*) Notice: Subject to any disclaimer, the term of this patent is extended or adjusted under 35 U.S.C. 154(b) by 1264 days.

This patent is subject to a terminal disclaimer.

(21) Appl. No.: 11/668,048

(22) Filed: Jan. 29, 2007

(65) Prior Publication Data

US 2008/0179179 A1 Jul. 31, 2008

(51) Int. Cl.
*C23F 11/00* (2006.01)
*G01N 17/04* (2006.01)

(52) U.S. Cl.
USPC ............... 422/53; 422/11; 204/404; 204/408; 204/409

(58) Field of Classification Search
USPC ............... 422/53; 204/164, 408; 324/72, 72.5
See application file for complete search history.

(56) References Cited

U.S. PATENT DOCUMENTS

| | | | |
|---|---|---|---|
| 4,261,803 A | 4/1981 | Suhara et al. | |
| 4,269,717 A | 5/1981 | Slovinsky | |
| 4,574,071 A | 3/1986 | DeSilva et al. | |
| 4,648,043 A | 3/1987 | O'Leary | |
| 4,775,005 A | 10/1988 | Beyer et al. | |
| 4,830,757 A | 5/1989 | Lynch et al. | |
| 5,236,845 A | 8/1993 | Pierce et al. | |
| 5,238,846 A | 8/1993 | Aucutt | |
| 5,243,297 A | 9/1993 | Perkins et al. | |
| 5,268,092 A | 12/1993 | Eden | |
| 5,332,494 A | 7/1994 | Eden et al. | |
| 5,342,510 A * | 8/1994 | Eden et al. ................. | 210/96.1 |
| 5,348,664 A | 9/1994 | Kim et al. | |
| 5,422,014 A | 6/1995 | Allen et al. | |
| 5,470,484 A | 11/1995 | McNeel | |
| 5,747,342 A | 5/1998 | Zupanovich | |
| 5,855,791 A | 1/1999 | Hays et al. | |
| 6,068,012 A | 5/2000 | Beardwood et al. | |

(Continued)

FOREIGN PATENT DOCUMENTS

| | | |
|---|---|---|
| JP | 10213562 | 8/1998 |
| JP | 2003254503 | 9/2003 |

(Continued)

OTHER PUBLICATIONS

TBI-Bailey, pH/ORP Sensors for Process Monitoring, 1998, Elsag Bailey, p. 1-40.*

(Continued)

*Primary Examiner* — In Suk Bullock
*Assistant Examiner* — Robert Eom
(74) *Attorney, Agent, or Firm* — Edward O. Yonter

(57) ABSTRACT

A device for measuring oxidation-reduction potential at operating temperature and pressure in hot water systems is disclosed and claimed. The device includes a flow-through cell, an oxidation-reduction potential probe, a temperature detector, and an external pressure-balanced reference electrode assembly. Each component of the device works in conjunction with the other components and each has electrical connections that transmit signals to a controller. The controller calculates and determines adjustments to feedwater chemistry for the hot water system.

14 Claims, 9 Drawing Sheets

(56) References Cited

U.S. PATENT DOCUMENTS

| | | | |
|---|---|---|---|
| 6,077,445 | A | 6/2000 | Ascolese |
| 6,336,058 | B1 | 1/2002 | Fowee |
| 6,350,376 | B1 | 2/2002 | Imaoka et al. |
| 6,391,256 | B1 | 5/2002 | Moon et al. |
| 6,402,984 | B1 | 6/2002 | Nakajima et al. |
| 6,409,926 | B1 | 6/2002 | Martin |
| 6,418,958 | B1 | 7/2002 | Rossi et al. |
| 6,436,711 | B1 | 8/2002 | Davis et al. |
| 6,510,368 | B1 | 1/2003 | Beardwood et al. |
| 6,566,139 | B2 | 5/2003 | Davis et al. |
| 6,587,753 | B2 | 7/2003 | Fowee |
| 6,609,070 | B1 | 8/2003 | Lueck |
| 6,620,315 | B2 | 9/2003 | Martin |
| 6,813,532 | B2 | 11/2004 | Eryurek et al. |
| 7,141,175 | B2 | 11/2006 | Verma |
| 7,208,117 | B2 | 4/2007 | Hays et al. |
| 2003/0004681 | A1 | 1/2003 | Fandrich et al. |
| 2006/0006122 | A1 | 1/2006 | Burns et al. |
| 2006/0169646 | A1 | 8/2006 | Andree et al. |
| 2006/0182651 | A1* | 8/2006 | Bailey et al. ............... 422/3 |

FOREIGN PATENT DOCUMENTS

| | | |
|---|---|---|
| JP | 2005233737 | 9/2005 |
| WO | 0159535 | 8/2001 |
| WO | 02101344 | 12/2002 |

OTHER PUBLICATIONS

Lvov et al., Advanced flow-through external pressure-balanced reference electrode for potentiometric and pH studies in high temperature aqueous solutions, 1998, Elsevier Science S.A., Journal of Electroanalytical Chemistry 443, p. 186-194.*

Buecker B., "Water Treatment: The Continuing Battle Against FAC," Power Engineering, Pennwell Publishing Co., Tulsa, OK, pp. 32-34, vol. 106, No. 9, Sep. 1, 2002.

Dedekind et al., "Oxygenated Feedwater Treatment at the World's Largest Fossil Fired Power Plant—Beware the Pitfall," Power Plant Chemistry, vol. 3, No. 11, Nov. 2001.

Filer, "Power Plant Chemistry Measurement Advancements: Oxidation Reduction Potential," Ultrapure Water, Nov. 1998.

Haag, J. et al., "On-Line Measurement of Redox and Corrosion Potentials in Water for PWR Steam Generators," Kraftwerkstechnik, Kraftwerkstechnik GMbH, Essen, DE, pp. 236-241, vol. 70, No. 3, Mar. 1, 1990.

Niedrach, L. W., "Electrodes for Potential Measurements in Aqueous Systems at High Temperatures and Pressures," Angewandte Chemie—International Edition in English, pp. 161-169, vol. 26, No. 3, Mar. 1987.

Uchino et al., "Study on the Practical Application of a Method for Corrosion Potential Measurement in a Water Quality Monitoring System used During Combined Water Treatment," PowerPlant Chemistry, pp. 511-517, vol. 3, No. 9, 2001.

Margulova, T. Kh. et al. "Conditions of dosing oxygen and hydrogen peroxide into the condensate of power units of supercriitical parameters." (Abstract), Teploenergetika (Moscow), 55-9, (6) 1977.

Pike, T.H. et al. "An Improved Method for Monitoring Low Concentrations of Volatile Oxygen Scavengers", Iwc, pp. 64-67, Jan. 2008.

Dooley, B. et al. "ORP—The Real Story for Fossil Plants", PowerPlant Chemistry, pp. 5-15, 5 (1), 2003.

* cited by examiner

Example of @T ORP numbers during oxygen reduction by mechanical and chemical means Test Conditions:
Start with deionized deaerated water
pH (RT) = 9.2 (caustic adjusted)
440 ml/min flowrate
All stainless steel system
Temperature = 250F Variables
System
Location
Catalysis
Metallurgy
Probe
Water chemistry
Thermodynamics
Kinetics
Flow
pH
etc

HIGH TEMPERATURE AND PRESSURE OXIDATION-REDUCTION POTENTIAL MEASURING AND MONITORING DEVICE FOR HOT WATER SYSTEMS

TECHNICAL FIELD

This invention relates to an oxidation-reduction potential measuring device. More specifically, the invention relates to an oxidation-reduction potential measuring and monitoring device used in conjunction with corrosion-inhibiting programs in hot water systems. The invention has particular relevance to an oxidation-reduction potential measuring and monitoring device, output signals of which are used to determine feed rates of chemicals that affect and control oxidation-reduction potential in industrial boiler systems.

BACKGROUND

Corrosion due to increased oxidation-reduction potential in hot water systems, such as industrial boilers, is a major concern. The affinity of oxygen for alloys used in the boiler water industry is the cause of many corrosion phenomena. This corrosion is a complex process that depends not only on the amount of oxygen in the system, but also on factors such as the water chemistry and metallurgy. For example, the presence of other species in the water could turn oxygen into an aggressive corrosive force, or could render the metallurgy passivated. Other important factors are temperature, pressure, fluid velocities, and operational practices. While oxygen might be the primary or essential component in the corrosion process, it might not be the only one.

The conventional means for reducing oxygen corrosion in hot water systems is to remove most of the molecular dissolved oxygen by mechanical and chemical means. The vast majority of the dissolved oxygen is reduced into the parts per billion range by the use of mechanical deaeration. The water is typically heated to above boiling temperature in a vented vessel leading to a decrease in dissolved oxygen solubility as the temperature increases. Flow dynamics and operational issues particular to deaerators leave parts per billion of dissolved oxygen in the water. Oxygen scavengers are chemicals used to reproducibly reduce dissolved oxygen values to low and constant values. Many of these scavengers also function as passivating corrosion inhibitors. Deaerators do not always work perfectly; if they did, a pure scavenger might never be needed, although a chemistry that enhances metal passivation would be a positive addition. In some cases, the oxygen scavenger is added as an insurance policy against the possibility that the deaerator might malfunction. The scavenger can also be added to combat air leakage into the system.

Traditionally, the amount of oxygen scavenger fed to boiler feedwater has been based on the amount of dissolved oxygen in the feedwater plus some excess amount of scavenger. The amount of excess scavenger fed is based on the desired residual scavenger concentration in the boiler feedwater or boiler water itself, which is a function of the excess concentration of scavenger and boiler cycles. There are several problems with this feed control scheme. The first is that there is no active control of the scavenger feed rate. High oxygen conditions could exist for long periods before a decrease in residual scavenger occurs and corrective action is taken.

A second issue is that the presence of residual scavenger in the boiler water simply does not mean that the system is being treated satisfactorily. Depending on the conditions (e.g., low temperature or short residence time) it is possible to have both high oxygen concentrations and sufficient scavenger in the feedwater at the same time. When this oxygen rich feedwater reaches the boiler, oxygen is flashed off with the steam leaving the unreacted scavenger in the boiler water. In an extreme case, the result may be an unacceptably high dissolved oxygen level in the pre-boiler and condensate systems while having expected residual concentrations of oxygen scavenger in the boiler itself.

In certain high-pressure boilers (once through) that use ultra-high purity water, a different approach has been taken. No oxygen scavengers are used. In fact small amounts of molecular oxygen are deliberately added to the feedwater. Oxygen (i.e., the oxidant) acts as the passivating agent for carbon steel under carefully controlled conditions of boiler water chemistry. Oxygen concentrations used are much less than the air saturated (8 ppm dissolved oxygen) values, thus some deaeration is used. It is often easier to deaerate to some extent prior to adding a controlled amount of oxygen.

Corrosion in industrial boiler systems typically occurs at operating (i.e., elevated) temperature and pressure. The most effective and accurate operational and control data is based on measurements taken under actual operating conditions. Gathering such data, which is indicative of corrosion stress on the system, at boiler feedwater temperature and pressure is difficult and seldom done. Traditionally, oxidation-reduction potential has been measured at room temperature and pressure in a sample taken from the system. Such room temperature measurements and other traditional measurements, such as dissolved oxygen, metallurgy-specific corrosion rate, or scavenger residual measurements, are incapable of detecting many corrosion events and stresses.

There thus exists an ongoing need for effectively measuring and monitoring oxidation-reduction potential at operating temperature and pressure in hot water systems. Such monitoring would enable proactive adjustment of feedwater chemistry (such as oxygen, oxygen scavengers, reducing agents, and oxidizing agents) rather than reactive adjustments after corrosion has already occurred. Continuous, real-time optimization of feedwater chemistry including an oxygen scavenger/passivation program would prevent corrosion problems that lead to lost steam production, downtime, reduced asset life, and higher operating costs.

SUMMARY

Accordingly, a device for measuring and monitoring oxidation-reduction potential at operating temperature and pressure ("ORP") in a hot water system is disclosed. In an embodiment, the device includes a flow-through cell, an electrode for sensing ORP in the system (referred to herein as "ORP probe"), a temperature detector, and a reference electrode. In a preferred embodiment, these components work in unison to measure and monitor ORP and temperature and to send these measured signals to a controller that determines feed rates of hot water system treatment chemicals, such as oxygen and/or oxygen scavengers. In a preferred embodiment, the measured potential (i.e., voltage difference) between the ORP probe within the flow-through cell and the reference electrode, preferably encased within an external pressure-balanced reference electrode assembly ("EPBRE"), indicates the ORP in a hot water system, such as an industrial boiler system.

In an aspect, the invention includes a device for measuring oxidation-reduction potential and temperature in a hot water system. In an embodiment, the device includes a flow-through cell having a plurality of ports including a first port, a second port, an inflow port, and an outflow port. In an embodiment, the device includes an ORP probe associated with the first port and having a connection to relay information to a controller. In an embodiment, the device further includes a temperature-dependent resistance sensor (sometimes referred to as "resistance temperature detector") associated with the first port and having a connection extending from the flow-through cell to a temperature detector electrical connection operable to relay information to a controller.

In one embodiment, the device also includes an external pressure-balanced reference electrode assembly associated with the second port. The assembly includes a porous frit on a first end of the assembly inside of the flow-through cell and a tube including an electrolyte solution and extending from the first end of the assembly to a second end of the assembly. The second end of the assembly is attached to a silver/silver chloride half-cell reference electrode having an electrical connection and operable to relay information to the controller.

In an embodiment, the device includes an ORP probe associated with the first port and having a first end and a second end. A platinum (or other noble metal) band is attached to the first end and resides within the flow-through cell. A corrosion-resistant wire (e.g., platinum) extends from the platinum band on the first end to the second end. The second end includes an electrical connection operable to relay information to a controller.

In another aspect, the invention includes a method of preventing corrosion in a hot water system by using the described device. The method includes determining an ideal ORP range for the hot water system. In an embodiment, the method includes measuring the ORP of the hot water system at operating temperature and pressure as the potential difference between the ORP probe and the reference electrode and measuring a temperature with the temperature detector. The measured potential and temperature is relayed to a controller system that interprets the measurements and determines whether the measured ORP is within the ideal ORP range. The method further includes adding an effective amount of oxygen or an effective amount of reductant to the feedwater of the hot water system, if the ORP is not within the ideal ORP range.

It should be understood that the disclosed device is capable of measuring and monitoring ORP and temperature in any still or flowing aqueous system or stream, but is primarily outfitted for the extreme conditions found in an operating hot water system or industrial boiler system. Temperatures may reach as high as about 260° C. and pressures may reach as high as about 3000 psi in such systems. In an embodiment, the ORP and temperature signals are continuously monitored. Alternatively, the signals may be monitored according to a timetable or intermittently monitored.

The measured ORP signal occurs naturally in the aqueous environment of the hot water system due to polarization of the ORP probe. Instead of using current to impress voltage, the specially designed ORP measuring and monitoring device allows passive measurement of ORP using free-floating potentials in the system. A suitable voltage signal-interpreting unit, such as a high input impedance voltmeter or other device, is typically needed to interpret or convert such potentials or voltage signals to a readable format. In a preferred embodiment, when installed vertically, the base of the EPBRE (i.e., the site of the multi-fitting housing, described in more detail below) is at ambient temperature, regardless of the system temperature; however the base remains at system pressure. In alternative embodiments, the base of the EPBRE may be in any position relative to the flow-through cell and its temperature may be at any level between ambient and system temperature, depending on the particular application.

It is an advantage of the invention to provide a device for measuring real-time oxidation-reduction potential in a hot water system at operating temperature and pressure.

It is another advantage of the invention to provide a device capable of measuring real-time oxidation-reduction potential in a hot water system at operating temperature and pressure and relaying the measured potential to a controller operable to adjust chemical feeding, such as oxygen or oxygen scavenger, into the feedwater of the hot water system.

Another advantage of the invention is to provide a device for measuring real-time oxidation-reduction potential in a hot water system at operating temperature and pressure and providing an operator with the output data for adjustment of chemical feeding, such as oxygen or oxygen scavenger, of the feedwater of the hot water system.

It is a further advantage of the invention is to provide a device capable of offering a novel and efficient approach to preventing corrosion in a hot water system.

An advantage of the invention also includes providing a device that simultaneously or concurrently measures oxidation-reduction potential and temperature of a hot water system at operating temperature and pressure.

Another advantage of the invention is to provide accurate and high-sensitivity measurements to detect corrosion events in hot water systems that cannot be detected with traditional room temperature measurement systems.

An additional advantage of the invention is to provide a method of measuring oxidation-reduction potential in hot water systems at high temperature and pressure thus allowing quick and accurate response to corrosion stresses in the system.

It is yet another advantage of the invention to provide a method of using the device herein described to prevent corrosion in a hot water system by measuring an oxidation-reduction potential of the hot water system at operating temperature and pressure and relaying the measured potential to a controller operable to adjust an oxygen feed or an oxygen scavenger feed into the feedwater of the hot water system.

A further advantage of the invention is to enable early detection of feedwater corrosion stresses that permits proactive adjustments to real-time oxygen and/or oxygen scavenger levels thus allowing optimization of such levels.

Additional features and advantages are described herein, and will be apparent from, the following Detailed Description and Figures.

DETAILED DESCRIPTION

Figure 1:
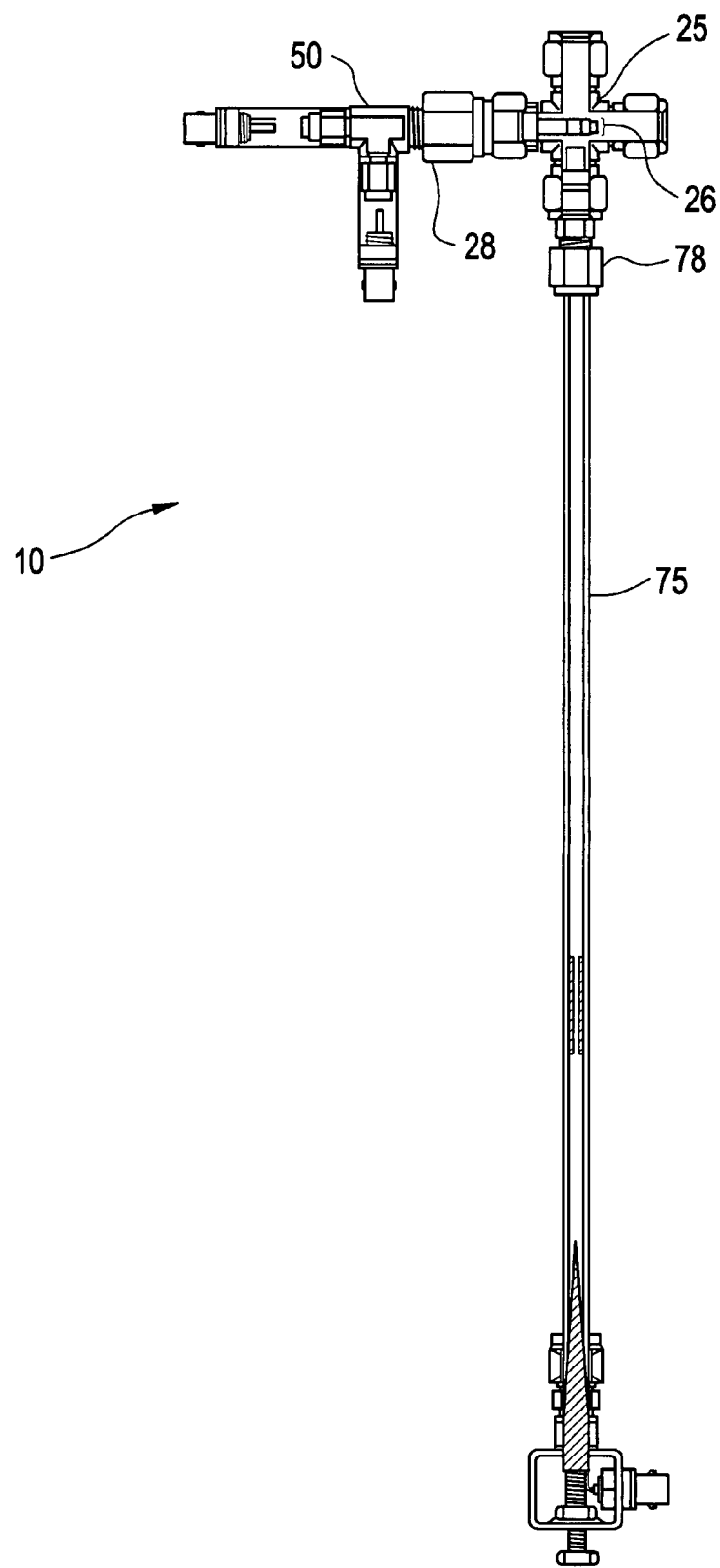
FIG. 1 is a side view of an embodiment of oxidation-reduction potential measuring device 10, shown with flow-through cell 25, union tee 50, and external pressure-balanced reference electrode assembly 75.

As used herein, "hot water system" refers to any system where hot water is in contact with metallic surfaces. "Hot water" means water having a temperature from about 37° C. up to about 370° C. The hot water system may operate at or below atmospheric pressure or a pressure up to about 3,000 psi. A preferred hot water system is an industrial boiler system, which typically has a water temperature of about 90° C. to about 260° C. and pressures reaching as high as about 3,000 psi.

"ORP," "ORP measurement," "measured ORP," or like terms refer to oxidation-reduction potential measurements taken at operating temperature and pressure. In an embodiment, the term encompasses concurrently measured and relayed temperature signals.

"Controller system" and similar terms refer to a manual operator or an electronic device having components such as a processor, memory device, cathode ray tube, liquid crystal display, plasma display, touch screen, or other monitor, and/or other components. In certain instances, the controller may be operable for integration with one or more application-specific integrated circuits, programs, or algorithms, one or more hard-wired devices, and/or one or more mechanical devices. Some or all of the controller system functions may be at a central location, such as a network server, for communication over a local area network, wide area network, wireless network, internet connection, microwave link, infrared link, and the like. In addition, other components such as a signal conditioner or system monitor may be included to facilitate signal-processing algorithms.

In one embodiment, the control scheme is automated. In another embodiment, the control scheme is manual or semi-manual, where an operator interprets the signals and determines feedwater chemistry, such as oxygen or oxygen scavenger dosage. In an embodiment, the measured ORP signal is interpreted by a controller system that controls an amount of oxygen or oxygen scavenger to introduce to the system to keep the measured ORP within a determined range. In an embodiment, the controller system also interprets measured temperature to determine the amount of oxygen or oxygen scavenger to add, if any. The temperature detector might also be used for information purposes, such as in alarm schemes and/or control schemes. It should be appreciated that the control scheme may incorporate pump limiters, alarming, intelligent control, and/or the like, based off further inputs, such as pH, dissolved oxygen levels, and other waste constituents.

In a preferred embodiment changes and adjustments to feedwater chemistry includes adding oxygen or one or more oxygen scavengers to the feedwater. By definition, oxygen scavengers are reducing agents (reductants), although not all reducing agents are necessarily oxygen scavengers. Reducing agents, suitable as oxygen scavengers, satisfy the thermodynamic requirements that an exothermic heat of reaction exists with oxygen. For practical applications, reasonable reactivity is required at low temperatures. That is, there should be some favorable kinetics of reaction. Furthermore, other changes and adjustments to feedwater chemistry, such as for system control and corrosion control, may include adding other oxidizing agents (oxidants) or other reducing agents (reductants).

It is also highly desirable that the reducing agent and its oxidation products are not corrosive and do not form products that are corrosive when they form in steam generating equipment. Typically, oxygen scavengers function optimally in certain pH ranges, temperatures, and pressures, and are also affected by catalysis in one way or another. The selection of the proper oxygen scavengers for a given system can be readily determined based on the criteria discussed above.

Preferred reductants (i.e., oxygen scavengers) include hydrazine, sulfite, carbohyrazide, N,N-diethylhydroxylamine, hydroquinone, erythorbate, methyl ethyl ketoxime, hydroxylamine, tartronic acid, ethoxyquin, methyltetrazone, tetramethylphenylenediamine, semi-carbazides, diethylaminoethanal, 2-ketogluconate, N-isopropylhydroxylamine, ascorbic acid, gallic acid, and hydroxyacetone.

Terms such as "coupler," "fitting," "nut," and the like as used herein are not intended to be differentiating, rather they are intended to generally describe and represent a similar type of fastener mechanism. Such terms are used for convenience and not due to a structural or functional limitation. Any suitable mechanism of attachment may be used for described couplers, fittings, and other fasteners or connectors. Typically, the attachment mechanisms are designed to withstand the temperatures and pressures encountered in a hot water system. To aid in sealing any of the couplers, fittings, etc. herein described, sealing agents such as fluoroelastomer (as used herein referring to flouroelastomers such as PTFE, TFE, FEP) tape, liquid fluoroelastomer, plumber's putty, silicone, or other suitable sealing agent may be used. Further, reference to a fitting as "high-pressure" is not intended to distinguish that fitting from others herein described, as each fitting is chosen depending on the particular hot water system characteristics.

Representative, nonlimiting examples of fittings, couplers, connectors, junctions, nuts, bolts, and the like herein described include NPT fittings, quick release NPT fittings, AN-style fittings, flared fittings, compression-type fittings (such as those utilizing ferrules), or any other suitable couplers, adaptors, fittings, or fasteners. Welding, brazing, gluing (e.g., cyanoacrylate, resin, or other suitable adhesive), or other type of permanent or semi-permanent attachment is also contemplated for some applications. Any suitable size, shape, material, etc. of the coupler, fitting, connector, adaptor, or junction may be used and is determined based upon the characteristics and demands of the particular application.

Certain electrical connections, such as cathodic and anodic connections, are provided herein in accordance with embodiments of the invention. In an embodiment, an ORP probe includes a cathodic connection and a reference electrode includes an anodic connection. Such connections are so named for convenience and by convention. In alternative embodiments, the poles for these connections may be transposed or switched, where, for example, the reference electrode is the cathodic connection and ORP probe is the anodic connection.

In one embodiment, all described electrical interfaces or connections associated with those interfaces (i.e., connections for the ORP probe, reference electrode, temperature detector) include a BNC-type connector. Alternatively, the connections may include other types of RF connectors, TNC-type connectors, banana plugs, crimp connectors, other types of electrical connectors, soldered connections, direct wire, or any other suitable electrical interface or connection.

Device Description

Referring to FIGS. 1 to 8, preferred embodiments of the ORP measurement and monitoring device (hereinafter referred to as the "ORP device") are illustrated and explained, where like numerals denote like components. In FIG. 1, an embodiment of ORP device 10 is shown with flow-through cell 25, sensor 26, union tee 50, and external pressure-balanced reference electrode assembly 75. The flow-through cell ("FTC") typically is the "foundation" of the ORP device to which other components are connected, including the temperature detector, sensor, and external pressure-balanced reference electrode assembly ("EPBRE"). In alternative embodiments, however, other components may be separate from the FTC and thus not directly connected to the FTC. In this embodiment, coupler 28 connects the FTC to the union tee and fitting 78 connects the FTC to the EPBRE.

Preferred fasteners include ¼ or ⅜ inch NPT fittings for coupler 28 and fitting 78. These connectors may be any suitable size and the examples herein are not intended to be limiting. For instance, a ⅜ inch female adaptor may be used for coupler 28, such as Part No. SS-6-TA-7-4, and reducing union Part No. SS-400-R-6BT may be used for fitting 78 (both available from Swagelok® in Solon, Ohio). In this embodiment, the EPBRE is illustrated "hanging" underneath and vertically with respect to the FTC. Such a vertical configuration is one embodiment and it should be appreciated that the EPBRE may be positioned at any angle relative to the FTC according to alternative embodiments. Preferably, the ORP device is installed so that the EPBRE points directly downward and towards the ground. This downward position maintains the EPBRE base at ambient temperature and ensures against bubble formation within the electrolyte solution (explained below).

Figure 2:
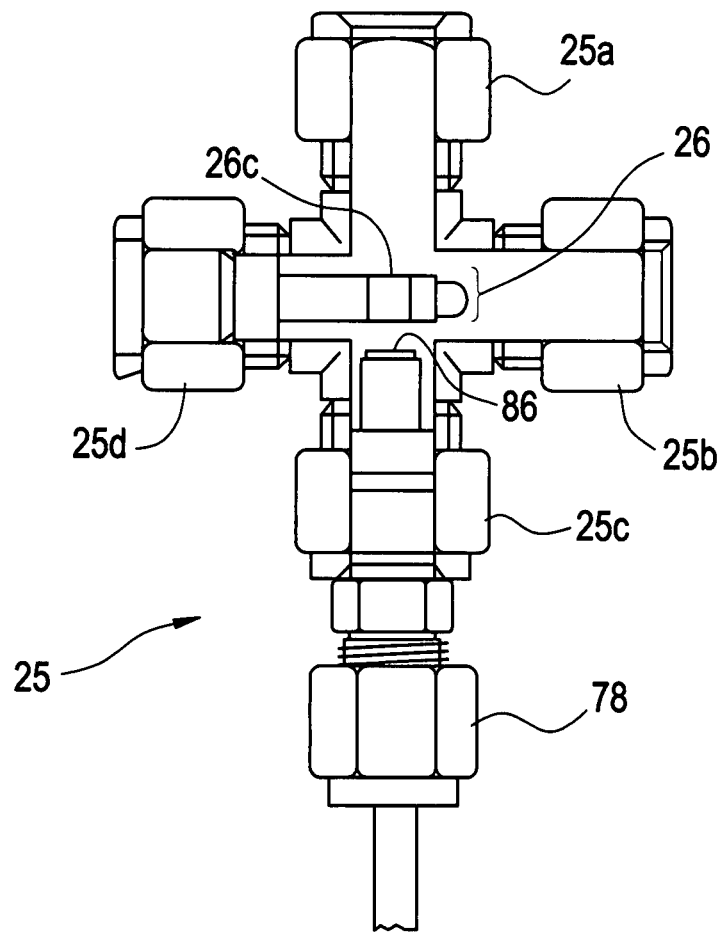
FIG. 2 is a schematic diagram of an embodiment of flow-through cell 25 having ports 25a, 25b, 25c, and 25d, sensor 26, and high-pressure fitting 78.

FIG. 2 illustrates a preferred embodiment of FTC 25. Though this schematic illustrates an embodiment having four ports, 25a to 25d, it is envisioned that the FTC may have additional ports such as for attaching or adding other components or for accommodating additional inflows and/or outflows. Some or all ports may be internally or externally connected or separate. An example of a preferred four-port FTC is ⅜ inch tube fitting, union cross Part No. SS-600-4 (available from Swagelok® in Solon, Ohio). In a preferred embodiment, the FTC is constructed of the ⅜ inch stainless steel cross and includes a bored-through configuration having 4 connected ports. It is contemplated that the bore size and other dimensions of the FTC may be chosen to accommodate any possible flowrate, as determined for each application. Preferred and typical flowrates include from about 50 ml/min to about 1,000 mL/min. More preferred flowrates are from about 100 ml/min to about 500 ml/min.

As shown in FIG. 2, inflow port 25b accommodates a water inflow from the hot water system and outflow port 25a directs the water back into the system or into a waste stream. In alternative embodiments, valves or other flow control devices may be used to control inflow and outflow into the FTC. One embodiment of such a flow control system is illustrated and explained in FIG. 8 below. It should be appreciated that the invention may include more than one inflow and/or outflow port, which may be configured to work in unison, independently controllable, or configured and operated in any suitable fashion. Port 25c in this embodiment includes high-pressure fitting 78 that connects the FTC to the EPBRE.

In an embodiment, sensor 26 is associated with the FTC and protrudes into near the center of the FTC. In one embodiment, the sensor includes an ORP probe. In another embodiment, the sensor includes a temperature detector. In a further embodiment, the sensor includes both the ORP probe and the temperature detector. In an embodiment, the temperature detector is a temperature-dependent resistance sensor, described in more detail below. When the water inflow contacts the ORP probe, for example, an ORP signal is produced between the ORP probe and the reference electrode that is relayed to the control system. The ORP probe is typically positioned in relation to porous frit 86, as explained in more detail below. Preferred materials for the porous frit include ceramic or electroceramic materials, such as zirconia, polymeric materials, the like, or any other suitable porous material. It is preferred that the porous frit be inert to hot water system processes and ORP signal measurement.

Figure 3:
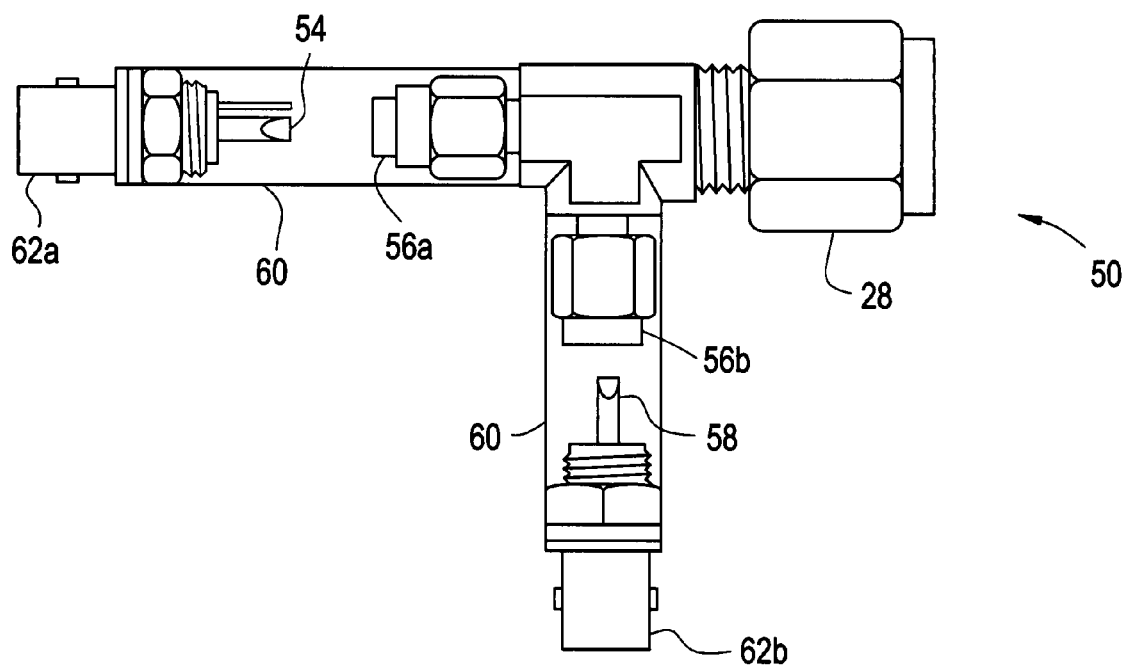
FIG. 3 is a schematic diagram of an embodiment of union tee 50 including coupler 28, temperature detector electrical connection 54, ferrules 56a and 56b, oxidation-reduction potential probe connection 58, L-bracket 60, and BNC connectors 62a and 62b.

In FIG. 3, an embodiment of union tee 50 is shown including coupler 28, temperature detector electrical connection 54, ferrules 56a and 56b, ORP probe connection 58, L-bracket 60, and BNC connectors 62a and 62b. Coupler 28 connects the FTC at port 25d (see FIG. 2) to the union tee. A preferred connector for coupler 28 is Part No. SS-6-TA-7-4 (available from Swagelok® in Solon, Ohio). In a preferred embodiment, the union tee includes two ⅛ inch tube connectors having a ¼ inch NPT connector on the remaining end that connects to coupler 28. In an embodiment, the union tee is mounted on or attached to the L-bracket or other stabilizing device or attachment. In alternative embodiments, the union tee may have other suitably sized fittings, which may be standard, metric, small, large, or any suitable configuration. One end of the union tee is connected to the flow-through cell according to an embodiment. Connected at the other two ends of the union tee are the temperature detector electrical connection and the ORP probe connection. Though any suitable union tee may be used, a preferred union tee is Part No. SS-200-3-4TMT (available from Swagelok® in Solon, Ohio).

Figure 4:
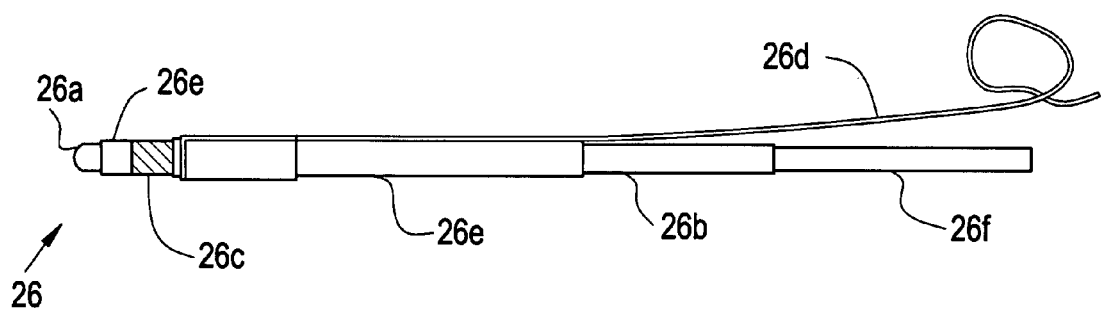
FIG. 4 illustrates an embodiment of sensor 26 having temperature detector 26a, insulating heat shrink 26b, noble metal band 26c, wire 26d, anchoring heat shrink 26e, and tube 26f.

FIG. 4 depicts an embodiment of sensor 26 having temperature detector 26a (at the "tip" of the sensor), insulating heat shrink 26b, noble metal band 26c, wire 26d, anchoring beat shrink 26e, and tube 26f. In this embodiment, tube 26f is a one end closed stainless steel tube having an outside diameter of about ⅛ inch and extending from about the center of the flow-through cell into the union tee. It should be appreciated that the tube may be of any suitable diameter, as determined for each application. The tube functions to provide support for noble metal band 26c ("band") and may include any corrosion-resistant material, such as stainless steel of any suitable composition, aluminum, other metals and plastics, and combinations thereof. In a preferred embodiment, the band functions as a passive ORP sensor. The ORP of the sample water is measured on the passive surface relative to the reference electrode. The band is located, in an embodiment, near the center of the FTC (as explained above for FIG. 2) and is in direct contact with the aqueous stream.

In a preferred embodiment, the temperature detector is a temperature-dependent resistance sensor (such as a PT100, PT200, PT1000, CU10, NI120). In one embodiment, the temperature-dependent resistance sensor is encased within tube 26f and is not directly exposed to the aqueous stream. The temperature detector may also include a standard thermocouple (such as type J, K, T, or E) or other temperature-sensing device according to alternative embodiments. In an embodiment, sensor 26 includes both an ORP probe having a noble metal band and a temperature detector, which are combined into one integrated component. In one embodiment, the sensor includes two wires, such as wire 26d, one of which transmits the ORP signal and the other the temperature signal. In another embodiment, the temperature detector includes a plurality of wires.

Alternative configurations for the temperature detector may include one, two, or more temperature detectors used either independently or in conjunction with one another. For example, if two temperature detectors are employed, one detector may be used to monitor temperature near the FTC while the other monitors the temperature near the reference electrode. Such configurations allow the user or operator of the ORP device to evaluate and calculate thermal potentials that might exist along the length of the EPBRE. This data would then be used to correct and deconvolute ORP values with respect to temperature differentials and potentials.

Figure 5:
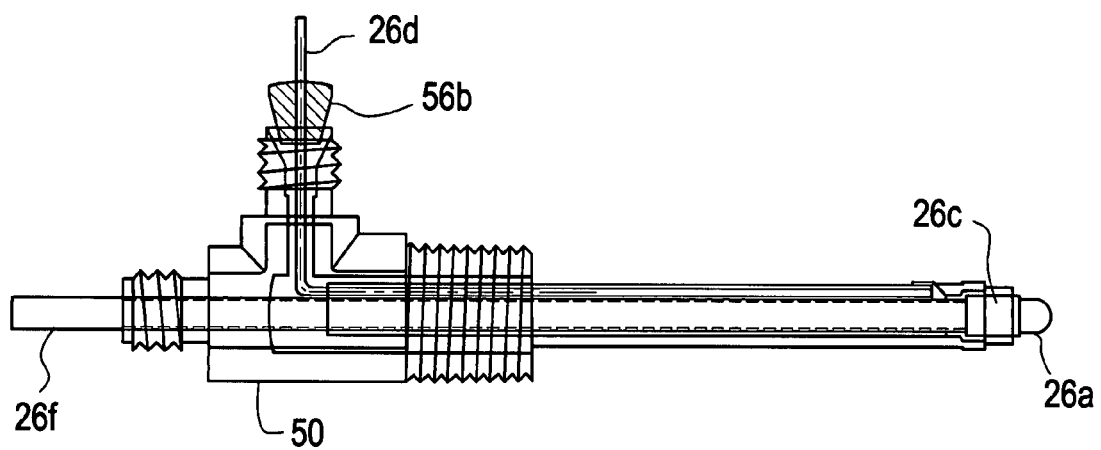
FIG. 5 is a cutaway view of the spatial relationship between several described components, including temperature detector 26a, noble metal band 26c, wire 26d, tube 26f, union tee 50, and ferrule 56b, according to a preferred embodiment.

The wire and band may include any noble metal, such as gold, silver, tantalum, platinum, rhodium, copper, and/or the like. Platinum is preferred. In an embodiment, any wire herein described may include an insulating material, such as plastic or fluoroelastomer, wrapped around such wire. Wire 26d is connected to the band and transmits an electrical signal to cationic connection 58. In an embodiment, another wire (not shown) transmits an electrical signal to temperature detector electrical connection 54 from an "active" portion of a resistance temperature detector that resides within the closed end of the tube at tip 26a. FIG. 5 illustrates a detailed cutaway view of the spatial relationship between several described components according to a preferred embodiment. In one embodiment, the tail end of sensor 26 protrudes through the union tee and into the space on the opposite side of the union tee from the FTC (as shown in FIG. 5). In this embodiment, the active portion of the temperature-dependent resistance sensor is located within the tube 26f at tip 26a.

Figure 6:
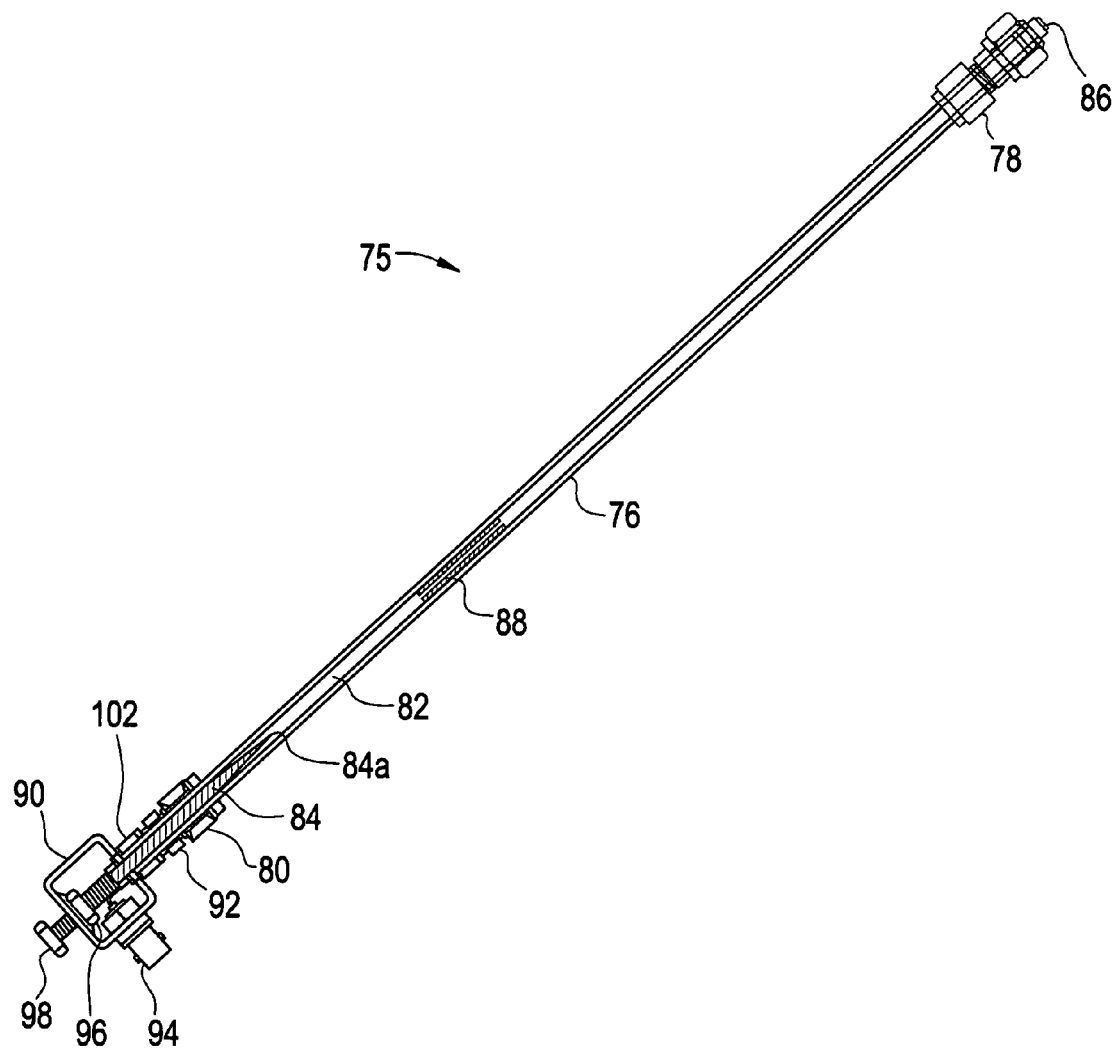
FIG. 6 depicts an embodiment of external pressure-balanced reference electrode assembly 75 including external tube 76, high-pressure fitting 78, high-pressure connector 80, internal tube 82, reference electrode 84, porous frit 86, insert 88, multi-fitting housing 90, reducing union 92, BNC connector 94, locking nut 96, bolt 98, and fastener 102.

A preferred embodiment of the reference electrode includes EPBRE 75, which acts to encase and thermally isolate the reference electrode. Illustrated in FIG. 6 is an embodiment of EPBRE 75 including external tube 76, high-pressure fitting 78, high-pressure connector 80, internal tube 82, reference electrode 84, porous frit 86, insert 88, multi-fitting housing 90, reducing union 92, BNC connector 94, locking nut 96, bolt 98, and fastener 102. The external tube in this embodiment is a ⅛ to ½ inch inner diameter stainless steel tube and houses the internal tube. In an embodiment, the EPBRE includes one or more inserts 88, which function to allow the internal tube to be separated to refresh, check, replace, refurbish, etc. the electrolyte solution, as explained in more detail below.

It should be appreciated that the external tube, the internal tube, and insert may be made of any suitable material of any suitable size, such as stainless steel, aluminum, fluoroelastomer, plastic, other suitable polymeric material, or other suitable metal. Preferably, the external tube is stainless steel (such as ¼ inch outside diameter 316 stainless steel tubing available from McMaster-Carr® in Elmhurst, IL) and the internal tube is fluoroelastomer having a tight fit with the external tube. In this example, external tube 76 is about 5 to about 25 inches long. Preferably, the external tube is about 10 to about 20 inches in length. The length of the external tube acts to thermally isolate the reference electrode (within the EPBRE) from the hot water system while maintaining about equal pressure between the hot water system and the reference electrode. It is made from any suitable tubing material, and any suitable diameter or length may be used.

Figure 7:
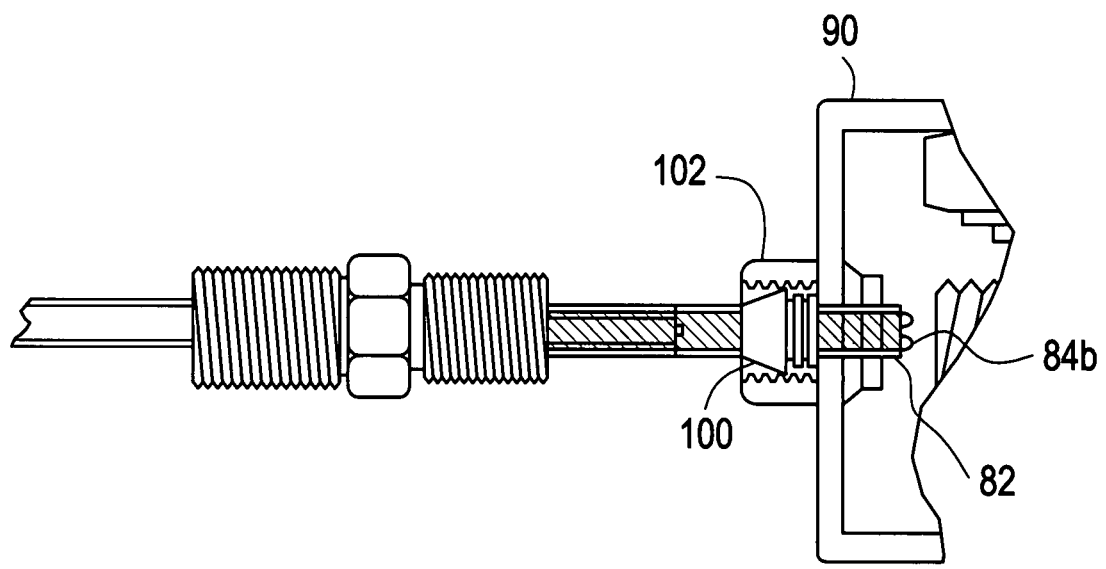
FIG. 7 shows an embodiment of multi-fitting housing 90 having sealed junction 100, fastener 102, internal tube 82, and reference electrode connection 84b.

An embodiment for the multi-fitting housing or "base" of the EPBRE is illustrated in FIG. 7, which includes sealed junction 100, fastener 102, and reference electrode connection 84b of the reference electrode. The sealed junction preferably includes a non metallic, multi-ferrule material. In this embodiment, the sealing material in the sealed junction comprises 3 separate fluoroelastomer ferrules secured with a 3/16 inch nut to the multi-fitting housing. An example of such a ferrule "assembly" includes Part No. T-303 and T-304 (available from Swagelok® in Solon, Ohio). In other embodiments, different types of seals and sealing materials may be used for the sealed junction. For example, the sealing material may include a gasket, elastomer, silicone, cork, flared fitting, rubber sleeve, o-ring, or any suitable seal or sealing material. In this embodiment, the ferrules function to place pressure on reference electrode 84, which is encased by the internal tube. Connector 80 is attached to reducing union 92 by, for example, standard stainless steel ferrules. The ferrules place pressure on the external tube thus holding it in place and providing a pressure-safe boundary.

The reference electrode is preferably about 2.5 to about 3.5 inches long and is tapered from tip 84a to sealed junction 100. In an embodiment, the reference electrode diameter remains constant from the sealed junction to reference electrode connection 84b. The reference electrode connection end is typically about 0.125 inches in diameter and the tip is typically about 0.01 inches in diameter. These diameters may be any suitable diameter according to alternative embodiments. The reference electrode (preferably a silver/silver chloride half-cell, where the tapered rod-shaped electrode includes silver with a silver chloride coating) extends from inside the internal tube (i.e., the tip is in contact with the electrolyte filling solution) to the end of the external tube and contacts the reference electrode connection. The reference electrode connection end includes a notch to accommodate a wire connecting the reference electrode to BNC connector 94 operable to transmit the electrical signal from the reference electrode to a receiver or controller, according to an embodiment. Bolt 98 acts to prevent the reference electrode from ejecting under system pressure and is typically made from any electrically isolating material, such as nylon, PVC, or other plastic.

Assembly

Though a multitude of methods for assembling the described ORP device exist, an exemplary method includes boring through union tee 50 with a ⅛ inch (or any size that matches the size of tube 26f) drill to allow insertion of tube 26f through the union tee. L-bracket 60 is then attached (e.g., welded) to the union tee and coupler 28 is attached to the FTC side of the union tee. In a subsequent step, the coupler will be used to affix the union tee to one of the ports, such as port 25c, on the FTC.

Forming the ORP probe (in an embodiment, noble metal band 26c) includes using a band (preferably platinum) having width of about 1/16 to about ½ inch (preferably about ¼ inch) and a diameter large enough to fit around tube 26f. Insulating heat shrink 26b is shrunk on tube 26f, leaving about ⅛ inch of the tube's closed-end exposed. A small portion of the band is then cut out and the now "C-shaped" band is tightly wrapped or folded around the insulating heat shrink. The cutaway portion or seam of the band should ultimately face away from porous frit 86 upon final assembly. One end of wire 26d is placed between the insulating heat shrink and the band, which is then crimped onto the insulating heat shrink. This crimping secures wire 26d between the insulating heat shrink and the band. The wire is typically further secured to the band through welding, soldering, etc. The wire is typically about 0.001 to about 0.01 inches in diameter and has a length (typically about 2.5 to about 4.5 inches) long enough to reach ORP probe connection 58.

In an embodiment, a temperature-dependent resistance sensor resides within tube 26f. For example, a 4-wire temperature-dependent resistance sensor is transformed into a 2-wire connector and linked to BNC temperature detector electrical connection 54. A small amount of heat shrink or other stabilizing material may be placed on the temperature-dependent resistance sensor to provide support and electrical isolation. The resistance sensor is then inserted into open end of tube 26f up to the closed-end of the tube. As the temperature of the outside surface of the tube changes relative to the aqueous stream, the heat change triggers resistance changes in the temperature-dependent resistance sensor, which, in turn, sends the appropriate electrical signal to the controller system.

Thus, tube 26f internally houses or encases a temperature-dependent resistance sensor and the ORP probe including noble metal band 26c resides on its outer surface, according to an embodiment. The tube is typically from about 3.5 to about 5 inches; however, any suitable length will work. Upon cutting the tube to length, and placing insulating heat shrink on a portion of the tube, the wire and band are secured in place. The insulating heat shrink may either cover nearly the entire tube or only partially cover the tube thus leaving a portion of each end of the tube exposed. For example, a small portion of the closed-end, such as ⅛ inch, and a slightly larger portion of the open end, such as about ½ inch to about 1 inch, may be exposed.

Another component, anchoring heat shrink 26e, acts to help hold the band and wire in place. In an embodiment, a first portion of the anchoring heat shrink is placed in front of the band (i.e., between the band and the closed-end tip of the tube) and a second portion of the anchoring heat shrink is placed on the other side of the band. The second portion of the anchoring heat shrink slightly overlaps the band and functions to further secure the band and the wire to tube 26f.

The assembled tube is then slid into the union tee and locked in place as follows. The wire extending from the band is inserted through the bottom portion of the union tee towards ferrule 56b and the end of the tube (also having the end of the temperature-dependent resistance sensor) is inserted into the union tee towards ferrule 56a. The ferrules are then locked and sealed. The wires extending from the ORP probe and temperature-dependent resistance sensor are then affixed to the BNC connectors, preferably by soldering. Electrical checks should be performed to ensure continuity between the band and the BNC fitting and to ensure the absence of conductivity between the band or wire and the rest of the assembly.

In one embodiment, multi-fitting housing 90 is typically made from stainless steel (other suitable metals, plastics, etc. are also contemplated) and has two main functions. The first function is to house the reference electrode electrical connection and the second function is to provide structural support to prevent reference electrode 84 from ejecting under system pressure. A reducing union nut is welded or otherwise attached to a first fitting of the multi-fitting housing. Locking nut 96 is secured to the inside of a second fitting of the multi-fitting housing. Bolt 98 is inserted into the locking nut to ensure the reference electrode is pressure-safe. BNC connector 94 attaches to a third fitting of the multi-fitting housing. Each of the above components may be secured using any suitable means, including welding, soldering, epoxying, and the like.

Assembling the EPBRE includes preparing the reference electrode, which has a taper extending across a length of the reference electrode, as explained above. The tapered portion of the reference electrode resides in the electrolyte solution. The reference electrode preferably is electro-chloridized by dipping it in about a 1 molar hydrochloric acid solution and passing about a 3.5 milliamp current across the reference electrode and a counter electrode for about 4 hours.

An exemplary method of electro-chloridizing the reference electrode includes setting up in a 1-liter glass cell with about 1 liter of 1 molar hydrochloric acid solution. Two carbon counter electrodes connected together serve as the counter electrode (to be connected to a potentiostat counter electrode lead). The reference electrode is preferably a silver rod as described above, which is suspended in the center of the glass cell. Both counter electrodes are 180 degrees apart at opposite edges of the glass cell. A typical potentiostat setup is: Current range 100 mA, mode galvanostat; Set scan setup: I1 0 A; delay 1 to 10 s; scan I1 mA/s; I2-8.3 in A (feed in as 0.083-mA); delay 2 6500; scan 2 10 s; I3 0A. Electrodes may be stored in a 0.1N KCl solution after electro-chloridizing.

In an embodiment, the internal tube includes one insert 88 that separates the internal tube into an upper portion and a base portion (and by functionality, also may separate the external tube into two portions). The upper portion is attached to one of the ports on the FTC and the base portion is attached to the base of the EPBRE. The two portions are connected using the insert. Such separability allows servicing the electrolyte solution within the internal tube.

To form the upper portion, a section of Teflon® heat shrink tubing (shrinks to about ⅛ inch outside diameter) about 12 inches long is heated to 345° C. in a kiln and cooled. Typically, a thin stainless steel (or other suitable material) tube placed inside of the Teflon® tubing provides structural support during the heating and cooling process. The support tube is removed after cooling. Porous frit 86 has, in this example, an outside diameter of about ⅛ inch, a length of about ½ inch, and a porosity of about 10% to about 20%. One end of the shrink tubing is trimmed to achieve a length of about 11.45 inches and the other end is slightly flared. The porous frit is pressed about ½ inch into the cut end of the shrunk tube, where about 0.05 inches to about 0.15 inches of the tip of the porous frit is typically left exposed beyond the internal tube. The about 1 inch long insert will fit inside of the flared end (up to about ½ inch). In an embodiment, the insert also undergoes a shrinking process as above. Alternatively, the insert is not shrunk and is a suitable size of Teflon® to be inserted into the heat shrunk Teflon® comprising the upper portion of the internal tube.

The base portion of the internal tube is shrunk and slightly flared as described above for the upper portion. In an embodiment, the end of the base portion that attaches to the multi-fitting housing is reinforced with additional Teflon® heat shrink tubing (or other similar material) and is flared at its top end to allow insertion of the remaining about ½ inch of the insert (i.e., that part of the insert which remains outside of the bottom part of the upper portion of the internal tube). The reinforcing material aids in providing support for the internal tube at reducing union 92. The electro-chloridized reference electrode is then pressed into the reinforced end of the base portion, with the tapered end of the reference electrode being inserted into the internal tube.

In one embodiment, internal tube 82 is filled with any concentration of electrolyte solution, such as NaCl, KCl, calomel (i.e., mercury(I) chloride or $Hg_2Cl_2$), the like, and combinations thereof. In an embodiment, filling the internal tube includes separating the tube via insert and filling an inner volume of the upper portion and the base portion with electrolyte solution using a long-needled syringe. The two portions are typically filled slightly past capacity resulting in menisci. When the two portions are connected, the electrolyte solutions combine thus leaving no air bubbles inside of the connected internal tube portions. The presence of air bubbles will cause inaccurate and open-circuit measurements. Preferably, the internal tube is filled with about 0.1 N KCl. Alternatively, the electrolyte solution includes about 0.001 N to about 3.8 N KCl. In other embodiments, the EPBRE does not have an internal tube, and the external tube is filled with the electrolyte solution. That is, one tube performs the function of the combination internal tube and external tube. In alternative embodiments, a plurality of tubes may be assembled or combined concentrically to perform the described function. In further embodiments, the EPBRE includes a standard hydrogen electrode or other suitable reference electrode.

Once the assembled internal tube is slid into external tube 76 to form a tube assembly, the bottom end of the tube assembly is attached to the multi-fitting housing and the top end of the tube assembly is attached to the FTC. A small part of the external tube (e.g., about 0.05 inches to about 0.25 inches) should remain exposed beyond the respective reducing unions on either end of the external tube. Assembling the reducing unions typically involves swaging, cold pressing, etc. the unions to form a seal.

According to an embodiment, assembling the multi-fitting housing includes welding or otherwise attaching fastener 102 to the multi-fitting housing. Sealed junction 100 fits into the fastener and provides a seal for the base portion of the internal tube. High-pressure connector 80, reducing union 92, and fastener 102 are assembled to attach the base portion to the multi-fitting housing. A small part of the reference electrode protrudes into the multi-fitting housing to allow connecting the reference electrode to BNC connector 94 with a wire or other conductive material. Locking nut 96 and bolt 98 are then assembled onto the multi-fitting housing to ensure that the reference electrode remains pressed into position under operating pressure.

Assembling the top of the tube assembly includes attaching high-pressure fitting 78 to one of the ports on the FTC. In an embodiment, a reducing union, such as Part No. SS-400-R-6BT (available from Swagelok® in Solon, Ohio) is used. In alternative embodiments, any suitable fastener, coupler, etc. may be used to attach the top of the tube assembly to the FTC. In an embodiment, the distance or spatial gap between porous frit 86 (the porous frit terminates the EPBRE at the FTC end) and the band is about 1/64 inch or greater. Preferably, the distance is about 1/8 inch to about 1/2 inch and most preferably the distance is about 3/16. Typically, the distance is about 1.5 times the diameter of the reference electrode connection end of the reference electrode and may be from about 1 to about 2 times that diameter. The end diameter preferably is about 1/100 to about 1 inch, more preferably about 1/8 inch to about 1/2 inch, and most preferably about 3/16 inch. In alternative embodiments, the end may be any suitable diameter, such as from about 1/100 inch or less to about several inches or more. In each embodiment, the end diameter is related to the spatial gap and calibration (explained below) of the ORP device includes adjustments to accommodate the spatial gap.

Calibration and Installation

Calibration of the ORP device includes, for example, checking the electrochemical potential of the EPBRE against a saturated potassium chloride standard half-cell. Under calibration conditions, the electrical connector normally (i.e., under operating conditions) connected to the ORP probe is connected to the EPBRE and the electrical connector normally connected to the EPBRE is connected to the standard known half-cell. Both electrodes should be immersed in a saturated potassium chloride solution. The potential difference between these two electrodes should be about 82 mV to about 92 mV if the ambient temperature is about 25° C. (preferably about 90 mV). Although the potential difference is a function of temperature, the effect of temperature is relatively small being about 2 mV from about 0° C. to about 50° C. Any significant variations from these figures typically indicate air bubbles in the electrolyte filling solution or a damaged reference electrode. A calibrated ORP device should provide a reading of zero millivolts when the connection normally used for the ORP probe is shorted to the connector normally used for the reference electrode.

Figure 8:
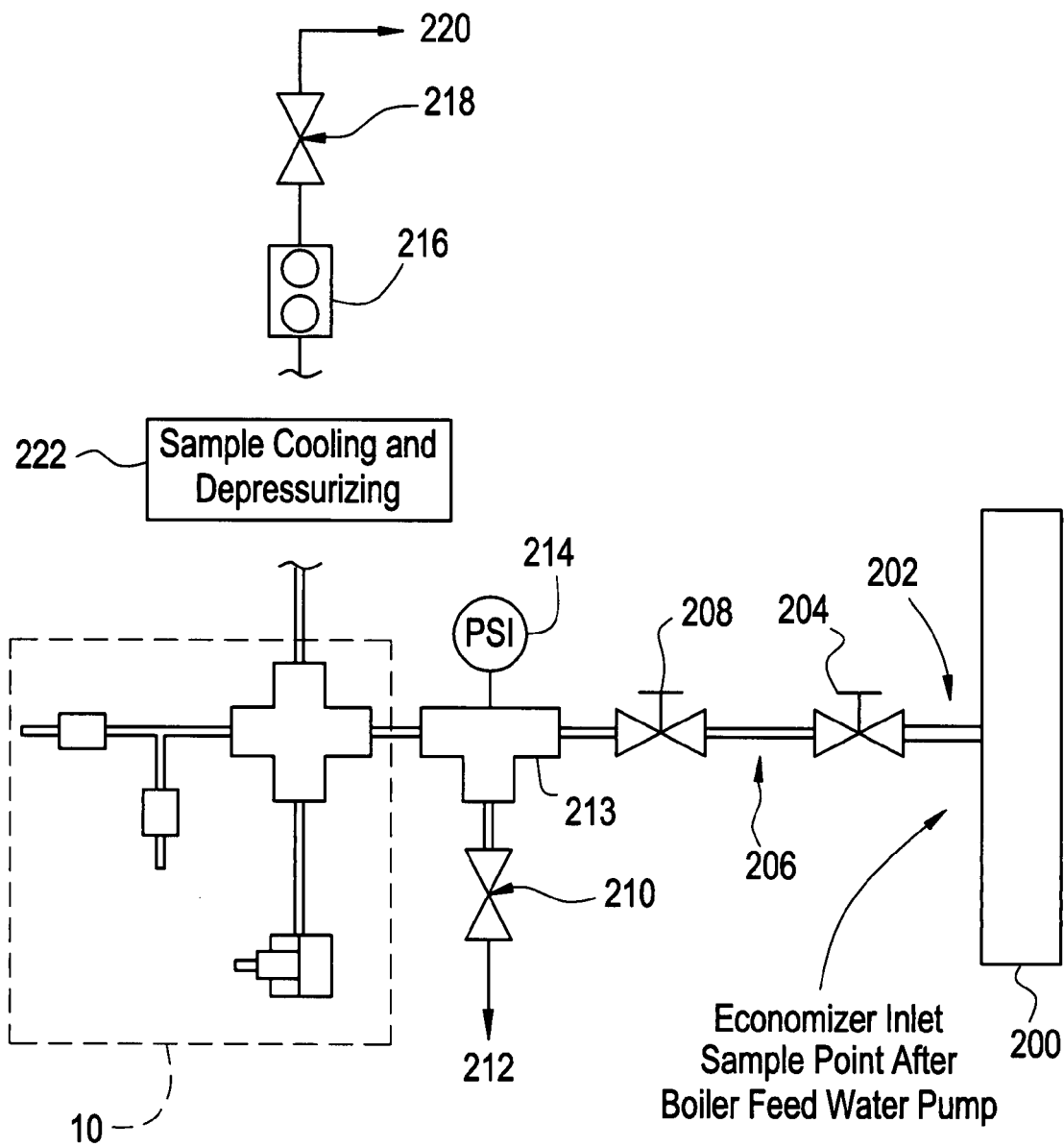
FIG. 8 illustrates an embodiment of oxidation-reduction potential measuring device 10 installed in hot water system 200 including feedwater sample outlet 202, lockable valve 204, transfer tube 206, isolation valve 208, vent valve 210, first free drain outlet 212, pipe tee 213, pressure gauge 214, flow meter 216, flow control valve 218, and second free drain outlet 220.

FIG. 8 depicts an embodiment of a typical ORP device installation in hot water system 200. It should be appreciated that one, two, or more ORP devices may be used in a hot water system. For example, certain plants use multiple deaerators where feedwater is routed to multiple boilers via multiple boiler feed pumps and backup systems. In these cases, several ORP devices installed at several different sample point locations may be needed. In an embodiment, ORP signals from one or more of these locations would be transmitted to a controller, which would calculate and determine any necessary changes to system chemistry.

The valves included in FIG. 8 are named for convenience. Any type of valve may used at each occurrence of a valve, such as 2-way, 3-way, Y-pattern, stopcock, needle, ball, globe, check, pilot, gate, butterfly, the like, or any suitable valve design. Further, the valves may be automated, manually controlled, or operated in any fashion as needed for particular applications to regulate the flowrate through the flow-through cell. In this embodiment, the hot water system includes lockable valve 204 that receives an online sample from feedwater outlet 202 and acts as initial point for introducing flow into the ORP device through transfer tube 206 and isolation valve 208. In this example, the feedwater outlet is attached to an economizer inlet, labeled as "Economizer inlet sample point after boiler feed water pump," in FIG. 8. Any suitable flowrate may be employed, as determined by the operator or controller system. Flowrates may be different and independently controlled for different parts of the system depicted in FIG. 8. Furthermore, constant flowrates typically provide more accurate ORP measurements. As explained above, flowrates are preferably from about 50 ml/min to about 1,000 ml/min. More preferred flowrates are from about 100 ml/min to about 500 ml/min.

Any size tubing or conduit of any suitable material may be used for the transfer tube, though 1/4 or 3/8 inch stainless steel tubing is preferred. Pipe tee 213 resides between the isolation valve and the ORP device. Also connected to the pipe tee is pressure gauge 214, which may be a simple gauge or a pressure sensing device/assembly capable of relaying pressure data to any receiver. In a typical installation, suitable insulation should be used on the components between the feedwater outlet and the ORP device to reduce heat loss and ensure stable temperatures are maintained in the ORP device. The sampled feedwater then flows through the ORP device, is optionally cooled and depressurized or alternatively is returned to the system or drained as waste through free drain 220.

In an industrial boiler application (e.g., conventional steam or utility boilers), the ORP device (and its components) is typically positioned close to the feedwater line sample takeoff (under operating temperature and pressure). With conventional steam boilers the position would preferably be after the main feed pump but prior to the economizer or after the deaerator. In electricity-generating utility boilers, the sample takeoff is typically prior to the deaerator. It should be appreciated that ORP device locations vary according to specific applications and configurations. S A complete audit of plant feedwater should typically be performed to determine where ORP measurements (i.e., "redox stress") would provide the greatest benefit for any particular application.

EXAMPLE

The foregoing may be better understood by reference to the following example, which is intended for illustrative purposes and is not intended to limit the scope of the invention.

Figure 9:
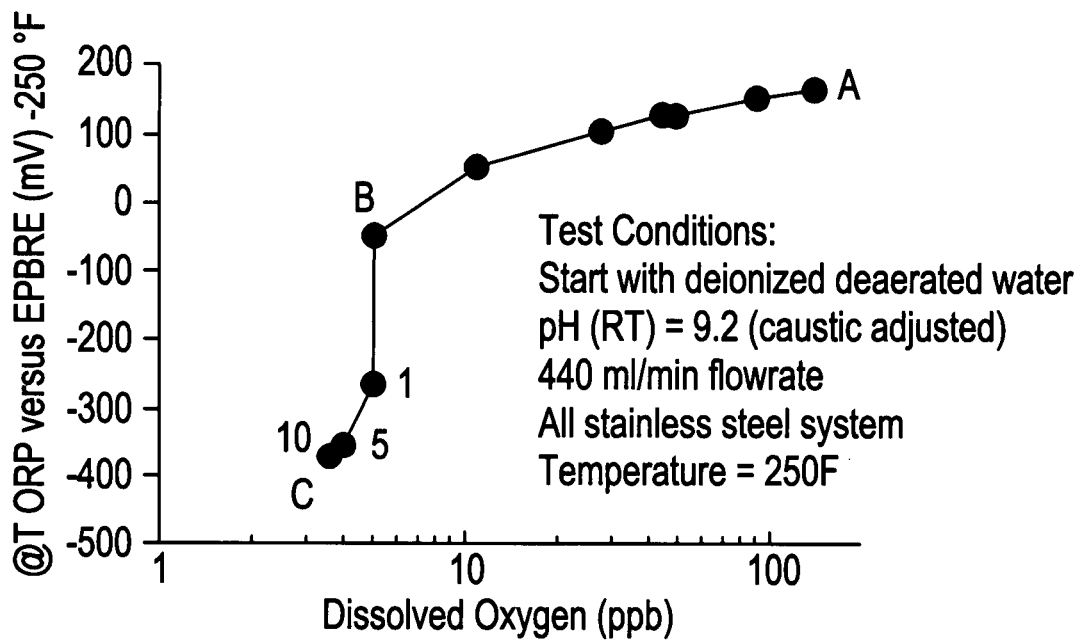
FIG. 9 shows multiple examples of high temperature and pressure ORP signal variations in a simulated industrial boiler feedwater system. The Y-axis shows the ORP numbers taken with the ORP device described herein. The X-axis shows the dissolved oxygen readings corresponding to each reading.

FIG. 9 shows multiple examples of high temperature and pressure ORP signal variations in a simulated industrial boiler feedwater system (@T ORP™). The Y-axis shows the ORP readings measured with the ORP device described herein. The X-axis shows the dissolved oxygen readings corresponding to each reading. The test conditions and some of the variables that might lead to differing ORP numbers are given in the legend for FIG. 9. In moving along the line segment from "A" to "B," an increasing amount of oxygen is removed from the system by mechanical deaeration. From point "B" to point "C," however, increasing amounts of reductant (carbohydrazide in this example) are added with the resulting decline in ORP values. In this case, the designation of "1" in the figure corresponds to 0.06 ppm (1×) of carbohydrazide added. Points "5" and "10" are 5× and 10× carbohydrazide addition. As can be seen, decreasing the amount of dissolved oxygen and increasing the amount of oxygen scavenger/reductant added has a significant effect on the measured ORP values taken at temperature and pressure.

It should be understood that various changes and modifications to the presently preferred embodiments described herein will be apparent to those skilled in the art. Such changes and modifications can be made without departing from the spirit and scope of the invention and without diminishing its intended advantages. It is therefore intended that such changes and modifications be covered by the appended claims.

The claimed invention is:

1. A device for measuring oxidation-reduction potential (ORP) and a temperature in a hot water system, the device comprising: (a) a flow-through cell having a plurality of ports comprising: a first port, a second port, an inflow port, and an outflow port; (b) a controller; (c) an integrated sensor component associated with the first port comprising: an ORP probe and a temperature detector, said integrated sensor component residing at least partially inside of the flow through cell, the ORP probe and temperature detector both further comprise at least one electrical connection operable to relay information to said controller, wherein the ORP probe is operable to measure ORP in the hot water system at operating temperature and pressure, and wherein the controller is operable to determine whether a real-time ORP is within an ideal ORP range and further operable to cause addition of an effective amount of oxygen or an effective amount of one or more reductants to a feedwater of the hot water system, if the real-time ORP is not within the ideal ORP range; and (d) an external pressure-balanced reference electrode assembly associated with the second port comprising: a tube containing an electrolyte solution having a first end residing at least partially inside of the flow-through cell and a second end, a porous frit disposed on said first end, and a multi-fitting housing attached to said second end, the multi-fitting housing having a silver/silver chloride half-cell reference electrode partially immersed in said electrolyte solution, and having an electrical connection operable to relay information to said controller.

2. The device of claim 1, wherein the measured ORP and the measured temperature are electronically transmitted to the controller.

3. The device of claim 1, wherein the flow-through cell further comprises a plurality of inflow ports and/or a plurality of outflow ports.

4. The device of claim 1, wherein the temperature detector is in fluidic communication with another of the said plurality of ports.

5. The device of claim 1, wherein the reference electrode is in fluidic communication with another of the said plurality of ports.

6. The device of claim 1, wherein the ORP probe comprises a noble metal.

7. The device of claim 6, wherein the noble metal is platinum.

8. The device of claim 1, wherein the temperature detector is a temperature-dependent resistance sensor.

9. The device of claim 1, further comprising a plurality of temperature detectors.

10. The device of claim 1, wherein the electrolyte solution comprises a potassium chloride solution from about 0.001 normal to about 3.8 normal.

11. A method of preventing corrosion in a hot water system by using the device of claim 1, the method comprising:
    (a) determining an ideal oxidation-reduction potential ("ORP") range for the hot water system;
    (b) measuring a real-time ORP of the hot water system at operating temperature and pressure;
    (c) measuring a real-time temperature of the hot water system;
    (d) relaying said measured ORP and said measured temperature to the controller;
    (e) determining whether the measured ORP is within the ideal ORP range; and
    (f) adding an effective amount of oxygen or an effective amount of one or more reductants to the feedwater of the hot water system, if the measured ORP is not within the ideal ORP range.

12. The method of claim 11, further comprising regulating a flowrate through the flow-through cell.

13. The method of claim 11, further comprising manually adding oxygen or reductant to the feedwater of the hot water system.

14. The method of claim 11, further comprising automatically adding oxygen or reductant to the feedwater of the hot water system.

* * * * *